US006146834A

United States Patent [19]

Schaad et al.

[11] Patent Number: 6,146,834

[45] Date of Patent: Nov. 14, 2000

[54] PCR PRIMERS FOR DETECTION OF PLANT PATHOGENIC SPECIES AND SUBSPECIES OF ACIDOVORAX

[75] Inventors: Norman W. Schaad, Meyersville, Md.; Wan-Yeob Song, Chonbuk, Rep. of Korea; Efstathios Hatziloukas, Thessaloniki, Greece

[73] Assignee: The United States of America as represented by the Secretary of Agriculture, Washington, D.C.

[21] Appl. No.: 09/393,877

[22] Filed: Sep. 10, 1999

[51] Int. Cl.[7] .......... C12Q 1/68

[52] U.S. Cl. .......... 435/6; 435/91.1; 435/91.2; 435/172.3; 435/177.3; 435/317; 536/27; 536/28; 536/29; 935/16; 935/17; 935/18

[58] Field of Search .......... 435/6, 91, 172.3, 435/177.3, 317; 536/27, 28, 29; 935/16, 17, 18

[56] References Cited

PUBLICATIONS

Gurtler et al., *Microbiology*, vol. 141, pp. 1255–1265, 1995.
Harvey et al., *J. Bacteriology*, vol. 170, pp. 1235–1238, 1988.
Islam et al., *J. Clinical Microbiology*, vol. 30, pp. 2801–2806, 1992.
Judd et al., *Applied Environmental Microbiology*, vol. 59, pp. 1702–1707, 1993.
Katz et al., *Am. J. Vet. Res.*, vol. 54, pp. 2021–2026, 1993.
Loughney et al., *Nuc. Acids Res.*, vol. 10, pp. 1607–1624, 1982.
Luneberg et al., *J. Clinical Microbiology*, vol. 31, pp. 1088–1094, 1993.
Prosen et al., *Phytopathology*, vol. 83, pp. 965–970, 1993.
Schaad et al., *Int. J. Syst. Bacteriol.*, vol. 28, pp. 117–125, 1978.
Schaad et al., *Phytopathology*, vol. 85, pp. 243–248, 1995.
Welsh et al., *Nucleic Acids Res.*, vol. 18. pp. 7213–7218, 1990.
Willems et al., *Int. J. Syst. Bacteriol.*, vol. 42, pp. 107–119, 1992.
Zavaleta et al., *Microbiology*, vol. 142, pp. 2105–2114, 1996.
Minsavage et al., *Ann. Mtg. Amer. Phytopathology*, Abstract 379, 1995.
Zeigler et al., *Intl. Rice Res. Newsletter*, vol. 14(1), pp. 27–28, 1989.
Song et al., *Phytopathology*, vol. 87(6), pp. 92, 1997.
Kim et al., *Seed Science & Technology*, vol. 24, pp. 571–580, 1996.
Shakya, D.D., *Korean J. Plant Pathology*(*Abstract*), vol. 3, p. 300, 1987.

*Primary Examiner*—Kenneth R. Horlick
*Assistant Examiner*—Janell E. Taylor
*Attorney, Agent, or Firm*—M. Howard Silverstein; John D. Fado; Evelyn M. Rabin

[57] ABSTRACT

We sequenced a 625 and 617 bp fragment of the inner spacer region of 16S-23S rDNA of a strain of *Acidovorax avenae* representing pathogens from several hosts, including foxtail, oats, corn, rice, millet, sugarcane, orchid, and watermelon and a strain of *A. avenae* subsp. *citrulli* pathogenic only to watermelon, respectively, for the purpose of designing PCR primers for their identification. These plant pathogens were previously considered as non-fluorescent pseudomonads and have been recently reclassified as *Acidovorax avenae* subsp. *avenae, A. avenae* subsp. *cattleyae,* and *A. avenae* subsp. *citrulli.* Several sets of primers were designed. Primers identified by SEQ ID NO:1 and SEQ ID NO:2 of subsp. *avenae* reacted with all strains of *A. avenae* subsp. *avenae* (previously named *P. avenae* or *P. alboprecipitans*) originating from foxtail, oats, corn, rice, sugarcane, and millet, *A. avenae* subsp. *cattleyae* from orchid, and *A. avenae* subsp. *citrulli* (previously named *P. pseudoalcaligenes* subsp. *citrulli*) from watermelon. Primers identified by SEQ ID NO:3, SEQ ID NO:4, SEQ ID NO:5, and SEQ ID NO:6 of subsp. *citrulli* reacted with all strains of *A. avenae* subsp. *citrulli,* but not with any other strain of subsp. *avenae.* None of fifty-three other bacteria tested reacted with either set of primers. The *citrulli-* specific primers should prove especially useful for specific, sensitive, and rapid detection of this serious seedborne pathogen of watermelon seeds.

30 Claims, 5 Drawing Sheets

Forward Primers:

5'-GTCGGTGCTAACGACATGG-3' (SEQ ID NO:1)

5'-GGAAGAATTCGGTGCTACCC-3' (SEQ ID NO:3)

5'-CCTCCACCAACCAATACGCT-3' (SEQ ID NO:5)

Reverse Primers:

5'-AGACATCTCCGCTTTCTTTCAA-3' (SEQ ID NO:2)

5'-TCGTCATTACTGAATTTCAACA-3' (SEQ ID NO:4)

5'-CATGCTCTTAGTCACTTGACCCTA-3' (SEQ ID NO:6)

Probe:

5'-CGGTAGGGCGAAGAAACCAACACC-3' (SEQ ID NO:7)

Fig. 1A

Forward Primers:

5'-GTCGGTGCTAACGACATGG-3' (SEQ ID NO:1)

5'-GGAAGAATTCGGTGCTACCC-3' (SEQ ID NO:3)

5'-CCTCCACCAACCAATACGCT-3' (SEQ ID NO:5)

Reverse Primers:

5'-AGACATCTCCGCTTTCTTTCAA-3' (SEQ ID NO:2)

5'-TCGTCATTACTGAATTTCAACA-3' (SEQ ID NO:4)

5'-CATGCTCTTAGTCACTTGACCCTA-3' (SEQ ID NO:6)

Probe:

5'-CGGTAGGGCGAAGAAACCAACACC-3' (SEQ ID NO:7)

```
Aac  GGTGAAGTCG TAACAAGGTA GCCGTATCGG AAGGTGCGGC TGGATCACCT CCTTTCT--G   58
Aaa  GGTGAAGTCG TAACAAGGTA GCCGTATCGG AAGGTGCGGC TGGATCACCT CCTTTCTAAG   60

                                                  SEQ ID:3
Aac  GAAAACAGCA TTCAATATTG AACGCCCACT CTTATCGGTT GTTGGAAGAA TTCGGTGCTA  118
Aaa  GAAAACAGCA TTCAATATTG AACGCCCACA CTTATCGGTT GTTGGAAGAA GTCGGTGCTA  120
                                                            SEQ ID:1
Aac  CCCGACATGG GTCTGGTAGC TCAGCTGGTT AGAGCACCGT CTTGATAAGG CTGG--GGTC  176
Aaa  AC-GACATGG GTCT-GTAGC TCAGCTGGTT AGAGCACCGT CTAGATAAGG CGGGGAGTCG  178

Aac  GTTGGTTCGA GCCCAACTAG ACCCACCAAA TCTTCCGAAC ATAAGATGCG AGGA--TCAG  234
Aaa  TTGGGTTCGA GCCCAACTCG ACCCACCAAA TCTTCCGAAC ATAAGATGCG AGGAATCAAG  238
                       tRNA^Ala
Aac  TGGGGGATTA GCTCAGCTGG GAGAGCACCT GCTTTGCAAG CAGGGGGTCG TCGGTTCGAT  294
Aaa  TGGGGGATTA GCTCAGCTGG GAGAGCACCT GCTTTGCAAG CAGGGGGTCG TCGGTTCGAT  298
                SEQ ID:5                  SEQ ID:7
Aac  CCCGTCATCC TCCA-CCAAC CAATACGCTC TGCGGTAGGG CGAAGAAACC AACACCAAAG  353
Aaa  CCCGTCATCC TCCACCCAAC CAATATGTCC TGCGGTAGGG CAAAGAAACT AACACCAAAG  358

Aac  CGGCTTCGCG -AGAGGCCTC TTTGTTGTTG GTCCGGTATA GACCGGATCA ATCGGCTGTT  412
Aaa  CGGCTTCGCG AAGAGGCCTC TTTGTTGTTG GTCCGGTATA GACCGGGTCA ATCGGCTGTT  418

Aac  CTTTAAAAAT TCATAGAGTC GAATCAGCGT TGCCGGCGGA AAGCAGGAAA CTGCA-CCGT  471
Aaa  CTTTAAAAAT TCATAGAGTC GAATCAGCGT TGCCGGCGGA AAGCAGGAAA CTGCATCCGT  478

Aac  GCCGCCGGTG ACAAAAATTT GATTGCGTCA AAACGAATAT TCAATT-GAG CGAAAGCTTG  530
Aaa  GCCGTCGGCA ACAAAAATTT GATTGCGTCC AAACGAATAT TCAATTGGAG CGAAAGCTGA  538
      "SEQ ID:4"
Aac  TTGAAATTCA GTAATGACGA ATTGTTCTC- TAGGTAGCAA TACCGCAAGA AGAATT-CAC  588
Aaa  TCGAAATTCA GTAATGACGA ATTGTTCTCT TAGGTAGCAA TACCCGAAGA AGAATTACAC  598

Aac  ATTACGGCA- TAACGCGCGA AGTGAAAGAC CTCGCAAGTC CTTGAAAGAA AGCGGAGATT  647
Aaa  ATTACGGCAT TAACGCGCGA TGTGAAAGAC CTCGCAAGTC CTTGAAAGAA AGCGGAGATG  658
                                "SEQ ID:6"      "SEQ ID:2"
Aac  TCTCGCTAGA GATTTCAAAG TTTTAGGGTC AAGTGACTAA GAGCATGTGG TGGATGCCTT  707
Aaa  TCTCGCAAGA GATGTCAA-- GTTATAGGTC AAGTGACTAA GAGCATGTGG TGGAT--CCT  714

Aac  GGCGATGATA GGCGACGAAA GACGTGATAG CCTGCGATAA   SEQ ID:8              747
Aaa  TGCGATGATA -GCGACGAAA GACGTGATAG CCTGCGATAA   SEQ ID:9              753
```

Fig. 1B

PCR PRIMERS FOR DETECTION OF PLANT PATHOGENIC SPECIES AND SUBSPECIES OF ACIDOVORAX

BACKGROUND OF THE INVENTION

1. Field of the Invention

*Acidovorax avenae,* formerly classified as *Pseudomonas avenae,* is a seedborne pathogen of several hosts including oat, corn, millet, wheat, sugarcane, rice, and melon (watermelon and cantaloupe). This invention relates to novel PCR primers which can be used to detect plant pathogenic *Acidovorax avenae* subspecies and to distinguish among the pathogenic subspecies, particularly to distinguish *A. avenae* subsp. *citrulli* from other subspecies.

2. Description of the Relevant Art

The bacterium *A. avenae* subsp. *avenae* causes bacterial stripe of rice, leaf blight of oats, red stripe disease of sugarcane and millet, and brown stripe of *Setaria italica.* The organism was originally described as *Pseudomonas avenae* by Manns in 1909 (Ohio *Agric. Exp. Stn. Res. Bull.* 210: 91–167) as the causal agent of leaf blight on oats in Ohio. Another organism, *P. alboprecipitans,* described by Rosen in 1922 on foxtail (*Ann. Mo. Bot. Gard.* 9: 333–402) and on corn in 1926 (*Phytopathology* 16: 241–267) was later shown to be synonymous with *P. avenae* (Schaad et al. 1975. *Int. J. Syst. Bacteriol.* 25: 133–137). On rice, the organism has been previously referred to as *P. setariae* or *P. panici* (Goto. 1964. *Bull. of Faculty of Agriculture,* Shizuoka University 14: 3–10) and on sugarcane as *P. rubrilineans* (Martin et al. 1989.), the causal agent of red stripe diseases of sugarcane (C. Ricaud et al. (Eds), Elsevier, The Netherlands, pp. 80–95). *Acidovorax avenae* subsp. *citrulli* causes bacterial blight and fruit blotch of watermelon and melon. The organism was originally described by Schaad et al. (1978. *Int. J. Syst. Bacteriol.* 28:117–125) in plant introduction breeding lines of watermelon in Georgia as *P. pseudoalcaligenes* subsp. *citrulli.*

Phylogenetically, *A. avenae* is included in the new "acidovorans" DNA-rRNA homology group (Willems et al. 1992. *Int. J. Syst. Bacteriol.* 42: 107–119). This group contains many pathogens previously classified in the non-fluorescent pseudomonad group, including *P. avenae* Manns 1909 (*Ohio Agric. Exp. Stn. Res. Bull.* 210: 91–167), *P. cattleyae* Savulescu 1947 (Pavarino. 1911. *Atti Accad. Lincei* 20:233–237), *P. pseudoalcaligenes* subsp. *citrulli* (Schaad et al. 1978, supra), and *P. rubrilineans* (Lee et al. 1925. Red Stripe Disease. Pamphlet of Hawaiian Sugar Planters Association). Recently, all of these bacteria have been reclassified as subspecies of *A. avenae,* i.e., *A. avenae* subsp. *avenae, A. avenae* subsp. *cattleyae,* and *A. avenae* subsp. *citrulli,* on the basis of the results of DNA—DNA hybridization, DNA-rRNA hybridizations, polyacrylamide gel electrophoresis of whole-cell proteins, and a numerical analysis of carbon assimilation tests (Willems et al., supra).

Presently, the only reliable method to identify the *A. avenae* pathogens, is to isolate them on agar media and confirm their presumptive identification by time consuming and expensive pathogenicity tests. For example, in rice, *A. avenae* subsp. *avenae* can be recovered from both diseased, or asymptomatic, apparently healthy seeds. However, identification is difficult, because the organism is frequently overgrown by other bacterial pathogens of rice, such as *Pantoea (Erwinia) herbicola, Burkholdera* (*Pseudomonas*) *glumae, B. fuscovaginae,* or *P. syringae* pv. *syringae.* These pathogens are recognized as producing distinct disease symptoms, but field diagnosis is very difficult. In such cases, detection and identification is based on pathogen isolation, through the use of semiselective media, and pathogenicity tests which discriminate between the various pathogens. However, the presence of coexisting epiphytes such as *P. putida* and *P. fluorescens* in/on rice seed makes isolation difficult. Furthermore, rice seedlings are difficult to grow and symptoms on seedlings are often non-discriminating. Several methods of identification of *A. avenae* subsp. *avenae* have been proposed including growth and isolation on semiselective agar media and serology (Shakya. 1987. *Korean J. Plant Path.* 3:300; Zeigler et al. 1989. *Intl. Rice Res. Newsletter* 14: 27–28). None have achieved much success. There is currently no reliable, routine method available for detecting *A. avenae* in rice seeds. More sensitive and specific methods are needed to confirm the identification, especially in seed health evaluations.

Similar problems exist for melons. Although originally described as a seedling disease, watermelon fruit blotch has emerged as a serious disease of mature fruit. Complete losses of production fields often occur due to fruit rot. Like most seedborne bacteria, control is based primarily on seed health testing. Because of the seriousness of watermelon fruit blotch, nearly all watermelon seed lots must be assayed for *A. avenae* subspec. *citrulli.* This involves soaking seeds and attempting to isolate the organism on agar media or inoculating plants with the seed soakate. Neither method is very efficient and both are relatively expensive. Little or no resistance to the pathogen exists.

Bacterial stripe causes great losses in rice seedling beds throughout Asia. Thus far, the disease has not been observed in the U.S. However, the potential risk of the dissemination of the bacterial stripe pathogen in international exchange of germplasm of rice, and also of corn and watermelon, is a serious concern. There is presently no way to separate infected seeds and contaminated seeds. Therefore, there is a need to develop reagents and methods for detecting *A. avenae* subspecies specifically, rapidly, and directly from biological samples. Such methods and reagents are valuable tools for monitoring natural disease spread, tracking the seedborne bacteria in field studies, and detecting the presence of the bacterium in seed lots entering *A. avenae* -free areas.

Polymerase chain reaction (PCR) has been shown to be highly sensitive and the method is commonly used to detect and identify bacteria. A PCR method has been described for detecting the pathogen *A. avenae* subsp. *citrulli,* in seeds; however, the primers are not unique and the method has not gained industry acceptance (Minsavage et al. 1995. *Ann. Mtg. Amer. Phytopath.* Abstract 379). Thus, there exists a need for specific primers and methods capable of specifically identifying and differentiating pathogenic *A. avenae* subspecies.

SUMMARY OF THE INVENTION

We have discovered oligonucleotide sequences which are capable of amplifying DNA fragments specific for identifying the two closely related pathogens when used in a simple and rapid PCR assay. One set of oligonucleotide sequences are specific for identifying all but one subspecies of *A. avenae*; another set is useful for selectively and specifically identifying the highly destructive watermelon fruit blotch pathogen, *A. avenae* subsp. *citrulli.* These two subspecies avenae and citrulli are phenotypically very similar and are very difficult to differentiate. In addition, two other sets of primers and probes specific for identifying *A. avenae* subsp. *citrulli* have been designed for the TaqMan (Perkin Elmer)

7700 detection system. One of these primers is the same as described for detecting *A. avenae* subsp. *citrulli* by classical PCR, whereas the other primers and probe are different.

In accordance with this discovery, it is an object of the invention to provide the novel oligonucleotides for use as primers for PCR assays for the specific detection and identification of plant pathogenic subspecies of *A. avenae.*

It is also an object of the invention to provide primers for the specific detection and identification of the watermelon fruit blotch pathogen, *A. avenae* subsp. *citrulli,* thereby differentiating *A. avenae* subsp. *citrulli* from other *A. avenae* subspecies.

It is another object of the invention to provide PCR assay methods utilizing the novel primers.

It is a further object of the invention to provide a screening method for distinguishing subspecies of *A. avenae* by utilizing two sets of primers.

It is an additional object of the invention to provide a method for assaying seeds for presence of *A. avenae* subsp. *citrulli* and for monitoring seed treatment protocols utilizing the novel primers.

It is an added object of the invention to provide a kit for use in the detection of *A. avenae* subspec. *citrulli.*

Other objects and advantages of the invention will become readily apparent from the following description.

BRIEF DESCRIPTION OF THE DRAWINGS

FIG. 1A shows the nucleotide sequence of the selected primers SEQ ID NO:1 and SEQ ID NO:2 of *Acidovorax avenae* subsp. *avenae* COA1 and the selected primers SEQ ID NO:3, SEQ ID NO:4, SEQ ID NO:5, SEQ ID NO:6 and the probe (SEQ ID NO:7) of *A. avenae* subsp. *citrulli* ATTC 29625. FIG. 1B shows the nucleotide sequence of the intergenic spacer region (ISR); the shaded area represents the ISR sequence of *Acidovorax avenae* subsp. *citrulli* (SEQ ID NO:8; Aac, upper) and *Acidovorax avenae* subsp. *avenae* (SEQ ID NO:9; Aaa, lower). The unshaded area represents $tRNA^{Ala}$ gene sequences. Sequences that are disclosed in the Sequence Listing as having SEQ ID NOs: 2, 4, and 6 are complementary to the reverse orientation of the sequences which are underlined and identified as "SEQ ID NO:2", "SEQ ID NO:4", and "SEQ ID NO:6" in FIG. 1B. SEQ ID NOs: 1, 3, 5, and 7 are also underlined and appear in FIG. 1B as they are disclosed in the Sequence Listing.

FIG. 2A: Lane 1, 100 bp ladder; Lane 2, *A. avenae* subsp. *avenae* (Aaa) ATCC 19822; Lane 3, Aaa 39463d; Lane 4, Aaa Nepal; Lane 5, Aaa 39462c; Lane 6, Aaa 39461g; Lane 7, *A. avenae* subsp. *citrulli,* (Aac) 40584 isolate B3; Lane 8, Aac 40565 A; Lane 9, Aac 40560 isolate 8; Lane 10, Aac 40565 b; Lane 11, Aac 40556 isolate 2; Lane 12, Aac 40582 isolate A1; Lane 13, Aac 40560 isolate 6; Lane 14, Aaa 39459 b; Lane 15, Aaa 39128 c; Lane 16, Aac 40582 isolate e/2; Lane 17, Aac 40582 isolate a1; Lane 18, Aac 40581 isolate B; Lane 19, Aac 40580 isolate A; Lanes 20 and 21, 100 bp ladder; Lane 22, Aaa ATCC 19822; Lane 23, Aac 40580 isolate A#2; Lane 24, Aaa 391230; Lane 25, Acc 40560 isolate 4; Lane 26, Acc 40580 isolate B; Lane 27, Acc 40584 isolate A2; Lane 28, Aac 40581 isolate A; Lane 29, Aac 40587; Lane 30, Aac, 405708 isolate A; Lane 31, Kihupi 40565; Lane 32, Aaa 39122 C; Lane 33, Aaa 39460 I; Lane 34, Pca 1; Lane 35, Pca 2; Lane 36, Pca 3; Lane 37, Pca 4; Land 38, Pca 5; Lane 39, Pca 6; Lane 40, 100 bp ladder. FIG. 2B: Lanes 1 and 18,100 bp ladder; Lanes 2 and 3, *A. avenae* subsp. *citrulli,* Aac 01; Lanes 4 and 5, *A. avenae* subsp. *cattleyae;* Lanes 6 and 7, *Burkholdera glumae;* Lanes 8 and 9, *A. avenae* subsp. *avenae* COA-1; Lanes 10 and 11, *A. avenae* subsp. *citrulli,* Aac 130; Lanes 12 and 13, *A. avenae* subsp. *cattleyae* PC-21; Lanes 14 and 15, *B. glumae* COG-2; and Lanes 16 and 17, *A. avenae* subsp. *avenae* COA-4.

DETAILED DESCRIPTION OF THE INVENTION

Figure 2A:
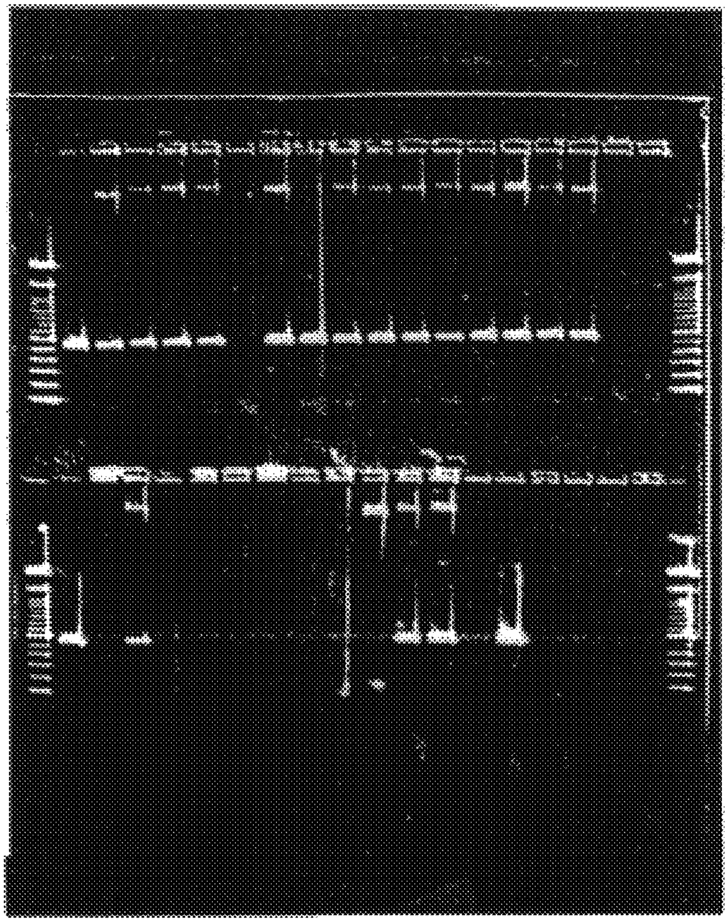
FIGS. 2A–2B are images of ethidium bromide stained gels showing a 550 bp PCR product formed by primers SEQ ID NO:1 and SEQ ID NO:2 (FIG. 2A) and a 450 bp PCR product formed by primers SEQ ID NO:3 and SEQ ID NO:4 (FIG. 2B.

Polymerase chain reaction (PCR) has been shown to be a highly sensitive and rapid method for detecting and identifying bacteria. The invention provides for PCR primers, methods, and kits useful for detecting subspecies of the pathogen *Acidovorax avenae* in or on seeds and further, for differentiating *A. avenae* subsp. *citrulli* from other *A. avenae* subspecies.

Strategy for obtaining specific primers for *A. avenae* subspecies

Several primers and primer sets have been identified as effective for amplifying particular *A. avenae* subspecies and differentiating between subspecies, when used in the standard PCR method (Mullis. 1987. U.S. Pat. No. 4,683,202) or the BIO-PCR method (U.S. patent application Ser. No. 08/344,085, herein incorporated by reference; Schaad et al. 1995. *Pytopath.* 85:243–248). Variations in length and sequences of the 16S-23S rDNA intergenic spacer region (ISR) of several bacteria have recently been targeted for use in discriminating among strains at the species and subspecies levels. These spacers are short stretches of DNA located between the 16S and 23S genes in prokaryotic rRNA loci and usually contain one or more tRNA genes. Elements important to transcription and noncoding of DNA that apparently are not functional should exhibit a considerable degree of sequence variation. Thus, such variable regions make sequences of ISRs good markers to measure short-term phylogeny. The characterization of the ISR of *A. avenae* and other bacterial pathogens of rice suggested that the ISR contained sequences unique to *A. avenae* (Kim et al. 1996. *Seed Sci. & Technol.* 24: 571–580). Therefore, the ISR of *A. avenae* was targeted as a possible source of DNA which would be specific for the different species and subspecies. In particular, unique PCR primers were derived from sequences of a fragment of the ISR of the 16S-23S rDNA for rapid identification of all those subspecies of *A. avenae* from oats, rice, corn, millet, wheat, sugarcane, orchid, and watermelon and for the specific detection of the subspecies *citrulli* from watermelon. These primers, when combined with BIO-PCR, should prove useful for sensitive detection of the pathogen in a seed health testing program for several diseases, including bacterial brown stripe of rice, leaf blight of oats, red stripe of sugar cane, bacterial leaf blight of corn and watermelon fruit blotch. Furthermore, rapid, conclusive, cost- and labor-efficient analysis can be performed when these unique primers and probes are combined with a BIO-PCR method employing the high throughput, real time TaqMan detection system.

A primer is preferably about eighteen to twenty-four nucleotides long. Primers can hybridize to a DNA strand with the coding sequence of a target sequence and are designated sense primers. Primers can also hybridize to a DNA strand that is the complement of the coding sequence of a target sequence; such primers are designated anti-sense primers. Primers that hybridize to each strand of DNA in the same location or to one another are known as complements of one another. Primers can also be designed to hybridize to a mRNA sequence complementary to a target DNA sequence and are useful in reverse transcriptase PCR.

The novel primers of the invention hybridize to a target DNA sequence of *A. avenae* subspecies located in the 16S-23S rDNA ISR of 950-bp. The primers are specific for *A. avenae* subspecies and do not hybridize to other closely related microorganisms. The primers can therefore be used in methods and kits for detecting subspecies of *A. avenae* in biological samples. The primers identified as SEQ ID NO:1 and SEQ ID NO:2 and the primer set comprising these primers are useful in an assay to detect the presence of *A. avenae* in a sample; specifically, any one or all of the subspecies, *A. avenae* subsp. *avenae, A. avenae* subsp. *cattleyae,* 8245 or *A. avenae* subsp. *citrulli.* The primers identified as SEQ ID NO:3 and SEQ ID NO:4 and the primer set comprising these primers distinguish *A. avenae* subsp. *citrulli* from *A. avenae* subsp. *avenae* and *cattleyae.* In addition, the primers of the invention are useful for employing BIO-PCR techniques for evaluating and monitoring the efficacy of treatments for eliminating the pathogenic *A. avenae* subspecies from seeds. Since BIO-PCR is based on detection of DNA from live cells, contaminating DNA from dead cells does not pose a problem. Detection of *A. avenae* subsp. *citrulli* can be further optimized by utilizing the primers identified as SEQ ID NO:4, SEQ ID NO:5, and SEQ ID NO:6 and the primer sets comprising these primers, namely, primer set SEQ ID NOs:5 and 4 or primer set SEQ ID NOs:5 and 6 in the BIO-PCR method, combining BIO-PCR with the TaqMan detection system and employing the probe identified as SEQ ID NO:7. TaqMan is a PCR-based assay that utilizes an oligo-nucleotide probe containing a "fluorescent reporter"-"fluorescence quencher" pair, wherein the quencher molecule of the probe is designed to be located close enough to the reporter molecule to ensure that the fluorescence of the reporter molecule is quenched. The binding site of the probe is located between the PCR primers used to amplify the target polynucleotide. Preferably, PCR is carried out using Taq DNA polymerase, AMPLITAQ (Perkin-Elmer, Norwalk, CN). During strand extension by Taq DNA polymerase, the annealed probe containing the reporter/quencher pair is digested by the 5'→3' exonuclease activity of taq polymerase. Digestion of the probe results in the reporter molecule becoming separated from the quencher molecule; thus, the quencher molecule is no longer close enough to the reporter molecule to quench the reporter molecule's fluorescence. Therefore, as more and more annealed probes are digested during amplification, the number of unquenched reporter molecules in solution increases, resulting in a stronger and stronger fluorescent signal being produced during consecutive cycles. This use of BIO-PCR together with the TaqMan automated real-time fluorescence detection system results in the detection of as few as 2 cfu/ml. The primers of the invention may also be useful as hybridization probes.

Preparation of Primers

Genomic DNA was extracted from cultures of *A. avenae* subsp. *avenae* strain COA1 and *A. avenae* subsp. *citrulli* strain 29625 in late logarithmic phase, as described by Prosen et al. (1993. *Pytopath.* 83: 965–970). The amplification of the ISR was performed using the known primers R16-1 and R23-2R and the method described by Kim et al., supra. For *A. avenae* subsp. *avenae*, the amplified full length 950-bp ISR product was cloned into pGEM7f (GIBCO BRL). The resulting clone, pOA3, containing the 950-bp full length ISR insert was then sequenced. For *A. avenae* subsp. *citrulli,* the amplified full length 950-bp ISR product was cloned into pCR2.1 with TA cloning kit (INVITROGEN). The resulting clone, pCIT7, containing a 950-bp insert of full length ISR, was then sequenced.

Figure 2B:
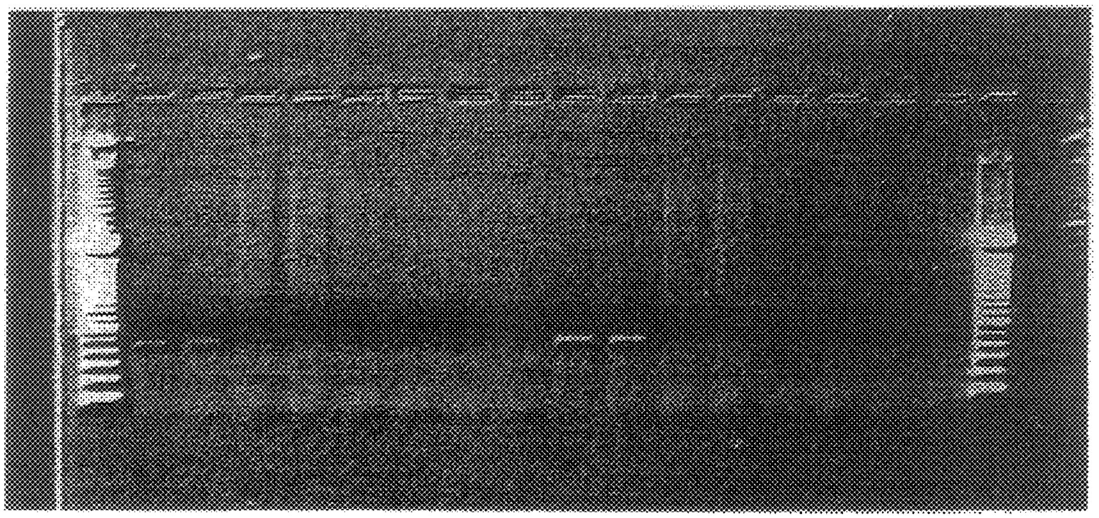

The sequencing of the cloned 16S-23S ISR fragment was performed by the dideoxy-chain termination method using ABI PRISM 310 Genetic Analyzer and Dye Terminator Cycle Sequencing Core Kit (Perkin Elmer, Foster City, Calif.) following the manufacturer's protocol (Sanger et al. 1977. *Proc. Natl. Acad. Sci. USA* 74: 5463–5467). From the ISR sequences, candidate primers were selected using the program OLIGO (National Biosciences, Hamel, Minn.) and synthesized commercially by GIBCO BRL (Frederick, Md.). The primers 5'-GTCGGTGCTAACGACATGG-3' (SEQ ID NO:1) and 5'-AGACATCTCCGCTTTCTTTCAA-3' (SEQ ID NO:2) of *A. avenae* subsp. *avenae* (FIG. 1A) and the primers 5'-GGAAGAATTCGGTGCTACCC-3' (SEQ ID NO:3) and 5'-TCGTCATTACTGAATTTCAACA-3' (SEQ ID NO: 4) of *A. avenae* subsp. *citrulli* (FIG. 1B) were used to amplify the ISR of 43 strains of *A. avenae*, 11 strains of *A. avenae* subsp. *citrulli,* four of *A. avenae* subsp. *cattleyae,* single strains of *A. avenae* subsp. *konjaci* and *A. facilis,* 26 other known bacteria, and 27 unknown bacteria isolated from seeds. The specificity of each set of primers is illustrated in Table 1, below, and in FIGS. 2A and 2B. As shown in Table 1, for primers SEQ ID NO:1 and SEQ ID NO:2, a PCR product of approximately 550 bp was obtained for all strains of *A. avenae* subsp. *avenae* and *A. avenae* subsp. *citrulli* and the ATCC strain of *A. avenae* subsp. *cattleyae.* Three strains of *A. avenae* subsp. *cattleyae* and the single strain of *A. avenae* subsp. *konjaci* were negative. All other bacteria, including 1–6 strains each of five other species of non-fluorescent pseudomonads (including 12 strains of Burkholderia), four fluorescent pseudomonads, two xanthomonads, two erwinea, and six strains of unknown bacteria from rice seed were negative. FIG. 2A also shows a 550 bp product obtained from strains of *A. avenae* subsp. *avenae* and *A. avenae* subsp. *citrulli.* Primers SEQ ID NO:3 and SEQ ID NO:4 produced a 450-bp product with all strains of *A. avenae* subsp. *citrulli* specifically (FIG. 2B); all other bacteria were negative.

The combination of BIO-PCR with TaqMan assay methodology is a more rapid and labor- and cost-effective assay than standard PCR or BIO-PCR where the additional identification step of Southern analysis is required. The BIO-PCR/TaqMan combination assay utilizing the primer set comprising primer 5'-CCTCCACCAACCAATACGCT-3' (SEQ ID NO:5) together with either primer 5'-TCGTCATTACTGAATTTCAACA-3' (SEQ ID NO:4) or primer 5'-CATGCTCTTAGTCACTTGACCCTA-3' (SEQ ID NO:6) as detected with the probe: 5'-CGGTAGGGCGAAGAAACCAACACC-3' (SEQ ID NO:7) results in the specific identification of *A. avenae* subsp. *citrulli.*

TABLE 1

Species and strains and results of PCR with primers SEQ ID NOS: 1 & 2 of *Acidovorax avenae* subsp. *avenae* and with the primers SEQ ID NOS: 3 & 4 of *A. avenae* subsp. *citrulli*

| Bacterial strains | No. | Host | Source[a] | PCR-Amplification SEQ ID NOS: 1 and 2[b] | PCR-Amplification SEQ ID NOS: 3 and 4[c] |
|---|---|---|---|---|---|
| *A. avenae* subsp. *avenae* (*Pseudomonas avenae*) | | | | | |
| COA1-3 | 3 | rice | 1 | + | – |
| ATCC 19860 | 1 | corn | 2 | + | – |
| PA135-138 | 4 | corn | 3 | + | – |
| 3307-8Pav | 2 | corn | 3 | + | – |
| 3403Pav | 1 | vasey-grass | 3 | + | – |
| 3406Pav | 1 | corn | 3 | + | – |
| 3431Pav | 1 | millet | 3 | + | – |
| Nepal | 1 | rice | 4 | + | – |
| 39123a | 1 | rice | 4 | + | – |
| 39459-39463 | 5 | rice | 4 | + | – |
| 30150-11 | 10 | rice | 5 | + | – |
| 311056-58 | 3 | rice | 5 | + | – |
| (*P. rubrilineans*) | | | | | |
| ATCC 19307 | 1 | sugar-cane | 2 | + | – |
| 931 | 1 | sugar-cane | 6 | + | – |
| 3107 | 1 | corn | 6 | + | – |
| 3111 | 1 | *Canna panicla* | 6 | + | – |
| XR119 | 1 | sugar-cane | 7 | + | – |
| XR3 | 1 | sugar-cane | 7 | + | – |
| (*P. setariae*) | | | | | |
| ATCC 19882 | 1 | rice | 2 | + | – |
| PS177 | 1 | rice | 7 | + | – |
| (*P. rubrisubalbicans*) | | | | | |
| XR105,106 | 2 | sugar-cane | 7 | + | – |
| *A. avenae* subsp. *citrulli* (*P. pseudoalcaligenes* subsp. *citrulli*) | | | | | |
| HIB, H17, B164 | 3 | water-melon | 8 | + | + |
| 1214, wwG, Mie3 | 3 | water-melon | 8 | + | + |
| ATCC 29625 | 1 | water-melon | 2 | + | + |
| 9217, 8408 | 2 | water-melon | 9 | + | + |
| 2576, 2578 | 2 | water-melon | 8 | + | + |
| *A. avenae* subsp. *cattleyae* | | | | | |
| ATCC 33619 | 1 | orchid | 2 | + | – |
| PC, 107, 112, 145 | 3 | orchid | 7 | – | – |
| *A. avenae* subsp. *konjaci* (*P. pseudoalcaligenes* subsp. *konjaci*) *Amorphophallus rivieri* | | | | | |
| ATCC 3399 | 1 | Konjac | 2 | – | – |
| *A. facilis* (*P. facilis*) | | | | | |
| ATCC 11228 | 1 | soil | 2 | – | – |
| *Burkholderia caryophylli* (*P. caryophylli*) | | | | | |
| PC131 | 1 | carna-tion | 7 | – | – |
| *B. cepacia* (*P. cepacia*) | | | | | |
| PC22, PC142 | 2 | onion | 7 | – | – |
| *B. gladioli* pv. allicola (*P. allicola*) | | | | | |
| PA7 | 2 | onion | 7 | – | – |
| PA16 | 1 | gladioli | 7 | – | – |
| *B. gladioli* pv. gladioli | | | | | |
| ATCC 25417 | 1 | gladioli | 2 | – | – |
| *B. glumae* (*P. glumae*) | | | | | |
| COG1-4 | 4 | rice | 1 | – | – |
| ATCC 33617 | 1 | rice | 2 | – | – |
| *P. fuscovaginae* | | | | | |
| Fed1259-3 IR VM | 1 | rice | 10 | – | – |
| *P. oryzicola* | | | | | |
| PO101 | 1 | rice | 7 | – | – |
| *P. syringae* pv. syringae | | | | | |
| Chi131-3 | 1 | rice | 1 | – | – |
| B728a | 1 | beans | 11 | – | – |
| *Xanthomonas oryzae* pv. oryzae | | | | | |
| CXO105, 211, 315 | 3 | rice | 1 | – | – |
| ATCC 35932 | 1 | rice | 2 | – | – |
| *X. oryzae* pv. oryzicola | | | | | |
| P501 | 1 | rice | 13 | – | – |
| ATCC 40972 | 1 | rice | 2 | – | – |
| *Pantoea herbicola* | | | | | |
| CEh1 | 1 | rice | 1 | – | – |
| ATCC 23375 | 1 | Milletia japonica | 2 | – | – |
| *P. syringae* pv. phaseolicola | | | | | |
| C199 | 1 | beans | 12 | – | – |
| *P. fluorescens* | | | | | |
| ATCC 13525 | 1 | | 2 | – | – |
| Other bacteria | | | | | |
| UPL1-6, UXL 1-7 | 13 | rice seeds | 14 | – | – |
| UWPL1-8, UWB 1-8 | 14 | water-melon seeds | 14 | – | – |

[a]1, W. Y. Song, Dept. Agric. Biology, Chonbuk National University, Chonju, Korea; 2, ATCC, American Type Culture Collection, Rockville, MD, USA; 3, ICPPB, International Collection of Plant Pathogenic Bacteria, USDA, Frederick, MD, USA; 4, L. E. Claflin, Dept. Plant Pathology, KSU, Manhatten, KS, USA; 5, C. Mortensen, Danish Govt. Inst. of Seed Pathology for Developing Countries, Copenhagen, DK; 6, MAFF, Ministry of Agriculture, Forestry and Fisheries of Japan, Tsukuba, Japan; 7, NCPPB, National Collection of Plant Pathogenic Bacteria, Harpenden, UK; 8, P. S. Randhawa, California Seed & Plant Lab., Elverta, California USA; 9, R. Latin, Dept. Plant Path., Purdue, Univ. West Lafayette, IN, USA; 10, F. Correa, CIAT, Cali, Colombia; 11, S. Hutchenson, Plant Biology Dept, Univ. Maryland, College Park, MD, USA; 12, T. Mew, IRRI, Manila, Philippines; 13, N. W. Schaad, ARS/USDA, Frederick, MD, USA; 14, this study.

TABLE 1-continued

Species and strains and results of PCR with primers SEQ ID NOS: 1 & 2 of *Acidovorax avenae* subsp. *avenae* and with the primers SEQ ID NOS: 3 & 4 of *A. avenae* subsp. *citrulli*

| | | | | PCR-Amplification | |
|---|---|---|---|---|---|
| Bacterial strains | No. | Host | Source[a] | SEQ ID NOS: 1 and 2[b] | SEQ ID NOS: 3 and 4[c] |

[b]Positive result means presence of 550 bp band and negative means no visible band in ethidium bromide stained agarose gel.
[c]Positive result means presence of 450 bp band and negative means no visible band in ethidium bromide stained agarose gel.

In brief, the DNA amplification process is carried out by (a) providing a biological sample comprising bacterial cells or extracted DNA for standard PCR or cells amplified by growing on an agar medium for BIO-PCR; (b) amplifying a target sequence of the DNA to provide DNA amplification products carrying the selected target DNA sequence; and (c) detecting the presence of the DNA amplification products as an indication of the presence of *A. avenae.*

The biological sample may either be bacteria cells or extracted genomic DNA. The biological sample may be a test sample suspected of containing bacterial cells, and thus the DNA of the bacterial cells, or a test sample containing extracted DNA.

The BIO-PCR method, disclosed in U.S. patent application Ser. No. 08/344,085, herein incorporated by reference, combines biological preamplification of the PCR target organism with enzymatic amplification of the PCR target. Briefly, the advantages of the BIO-PCR method, over those of the standard PCR assay, include the detection of live cells only, a 100–1000 fold increase in sensitivity, and elimination of PCR inhibitors associated with plant samples thereby eliminating false negatives. Sample processing can be further simplified by directly processing the samples comprising the expanded cells without further DNA extraction. However, even if a DNA extraction step is included, an advantage of the BIO-PCR methodology is that the DNA is extracted from a growing, viable population of cells or microorganisms. The enhanced sensitivity of the BIO-PCR method is particularly valuable, for example, in those screening situations where the monetary value of a particular seed type is high, and thus it is desirable to test the smallest quantity of seeds possible, and where among trading partners, there is zero tolerance or quarantine for contaminating pathogens.

The preamplification step involves a plating step on an agar growth medium (or a liquid medium) prior to PCR analysis. A single cell per 0.1 ml can be detected because the single cell multiplies into a colony containing over 1000 cells on the agar medium.

Bacteria are recovered from suspect seeds of rice and watermelon by first soaking 1000–2000 seeds in 0.02% TWEEN 20 solution (ratio of 5 ml/g) for 4 hours at 40° C., pipetting aliquots of 0.1 ml of the bacterial extracts either onto plates of general purpose agar media, such as, KB or nutrient agar (NA), or onto a semiselective medium such as EBB, described below, and then cloning. For BIO-PCR, each of five plates is washed three times with 1.0 ml of water and the resulting 14–15 ml of wash solution can be used for PCR-amplification with or without further DNA extraction or sample processing. Similarly, for standard PCR, either the DNA can be extracted or intact cells used. Since only pinpoint-size colonies are needed, incubation time ranges from only 10–15 hr for fast growing bacteria to 24–48 hrs for most plant pathogenic bacteria, depending on the media. Since the incubation time is short, few other bacterial colonies are present.

EBB medium is a preferred, semiselective medium to use for the preamplification step. The protocol for preparing the EBB Medium is as follows:

(1) Mix, per liter:

| | |
|---|---|
| $NH_4PO_4$ | 1.0 g |
| $MgSO_4.7\ H_2O$ | 0.2 g |
| KCl | 0.2 g |
| Yeast Extract | 0.3 g |
| Boric acid | 0.5 g |
| Brilliant blue R (10 mg/ml Stock) | 1.0 ml |
| Bromcreosol purple (15 mg/ml Stock) | 0.6 ml |
| Agar | 16.0 g |

(2) Autoclave and add, per liter:

10.0 ml 95% ethanol 1.0 ml Cycloheximide (200 mg/ml 95% ethanol Stock)

(3) Adjust pH carefully to 5.2 using 0.2 M HCl just before autoclaving. (If the pH falls below 5.0, do not use NaOH to readjust to 5.2 as NaOH will neutralize brilliant blue R.)

In the preferred method, the enzymatic amplification of the DNA sequence is by polymerase chain reaction (PCR), as described in U.S. Pat. No. 4,683,202 to Mullis, herein incorporated by reference. In brief, the DNA sequence is amplified by reaction with at least one oligonucleotide primer or pair of oligonucleotide primers that hybridize to the target sequence or a flanking sequence of the target sequence and a DNA polymerase to extend the primer(s) to amplify the target sequence. The amplification cycle is repeated to increase the concentration of the target DNA sequence. Amplified products are optionally separated by methods such as agarose gel electrophoresis. The amplified products can be detected by either staining with ethidium bromide or silver stain or by hybridization to a labeled probe, such as in TaqMan PCR which is based on real time hybridization. In an alternative embodiment, at least one probe that hybridizes to the amplified products is labeled with either a biotin moiety and/or a fluorescent moiety. The complexes are then bound to a solid support such as a bead, multiwell plate, dipstick or the like that is coated with streptavidin. The presence of bound hybrids can then be detected using an antibody to the fluorescent tag conjugated to horseradish peroxidase. The enzymatic activity of horseradish peroxidase can be detected with a colored, luminescent, or fluorimetric substrate. Conversion of the substrate to product can be used to detect and/or measure the presence of *A. avenae* PCR products.

Other methods of PCR using various combination of primers including a single primer to about three primers are known to those of skill in the art and are described in Maniatis (1989. *Molecular Cloning: A Laboratory Manual.* Cold Spring Harbor, N.Y.). Those methods include asymmetric PCR, PCR using mismatched or degenerate primers, reverse transcriptase PCR, arbitrarily primed PCR (Welsh et al. 1990. *Nucleic Acids Res.* 18: 7213–7218), or RAPD PCR, IMS-PCR (Islam et al. 1992. *J. Clin. Micro.* 30: 2801–2806), multiwell PCR (ELOSA) (Luneberg et al. 1993. *J. Clin. Micro.* 31: 1088–1094), and Katz et al. 1993. *Am. J. Vet. Res.* 54: 2021–2026). The methods also include amplification using a single primer as described by Judd et al. 1993. *Appl. Env. Microbiol.* 59: 1702–1708).

An oligonucleotide primer preferably has a DNA sequence that hybridizes under standard conditions for PCR to a sequence flanking one end of the DNA sequence to be amplified. In the use of a pair of oligonucleotide primers, each of the primers is distinct and has a different DNA sequence. The two distinct primers are directed at specific sequences on opposite strands and together define the segment to be amplified, i.e., they hybridize to sequences at either end of the target sequence. Design of primers and their characteristics have been described previously. The DNA sequences of the oligonucleotide primers are positive-sense (forward) 5'-GTCGGTGCTAACGACATGG-3' (SEQ ID NO:1), negative sense (reverse) 5'-AGACATCTCCGCTTTCTTTCAA-3' (SEQ ID NO:2), positive sense (forward) 5'-GGAAGAATTCGGTGCTACCC-3' (SEQ ID NO:3), negative sense (reverse) 5'-TCGTCATTACTGAATTTCAACA-3' (SEQ ID NO:4), or complements thereof, or mixtures thereof. The primers may also be degenerate primers that hybridize to the target DNA sequence under hybridization conditions for a primer of that size and sequence complementarity.

For the binding and amplification, the biological sample (bacterial cells or extracted DNA) is provided in an aqueous buffer formulated with an effective amount of a divalent cation which is preferable $MgCl_2$, preferably at a concentration of about 0.05–5 mM; an effective amount of DNA polymerase with Taq DNA polymerase being preferred in the form of native purified enzyme or a synthesized form such as AMPLITAQ (Perkin-Elmer), an effective amount of dNTPs as a nucleotide source, including, dATP, dCTP, dGTP, and dTTP, preferably in a saturating concentration, preferably about 200 $\mu$M per dNTP; and an effective amount of one or a pair of oligonucleotide primers. The reaction mixture containing the annealed primer(s) is reacted with a DNA polymerase at about 72° C. to about 94° C. for about 1–10 minutes, to extend the primers to make a complementary strand of the target gene sequence. The cycle is then repeated by denaturing the DNA strands with heat, annealing and extending, preferably for about 25–40 cycles, preferably about 30 cycles.

If designed properly, a single product results. This product is preferably about 450–550-kb in size, whose termini are defined by the oligonucleotide primer(s), and whose length is defined by the distance between the two primers or the length of time of the amplification reaction. The gene sequence then serves as a template for the next amplification cycle.

The amplified DNA product is optionally separated from the reaction mixture and then analyzed. The amplified gene sequence may be visualized, for example, by electrophoresis in an agarose or polyacrylamide gel or by other like techniques, known and used in the art.

The amplified gene sequence may be directly or indirectly labeled by incorporation of an appropriate visualizing label, as for example, a radioactive, calorimetric, fluorometric or luminescent signal, or the like. In addition, the gel may be stained during or after electrophoresis with a visualizing dye such as ethidium bromide or silver stain wherein the resulting bands by be visualized under ultraviolet light.

To prove the identity of the amplified DNA product, a Southern blot assay should be conducted. The amplified products are separated by electrophoresis on a polyacrylamide or agarose gel, transferred to a membrane such as a nitrocellulose or nylon membrane, reacted with an oligonucleotide probe, and stained as above. The amplified products may also be detected by reverse blotting hybridization (dot blot) in which an oligonucleotide probe specific to the gene sequence is adhered to a nitrocellulose or polyvinylchloride (PVC) support such as a multi-well plate, and then the sample containing labeled amplified product is added, reacted, washed to remove unbound substance, and a labeled amplified product attached to the probe or the gene sequence imaged by standard methods.

A major advantage of TaqMan PCR is that the technology is based on hybridization; therefore, a Southern blot assay is not needed. The DNA sequences of the oligonucleotide primers for TaqMan PCR are positive-sense (forward) 5'-CCTCCA CCAACCAATACGCT-3' (SEQ ID NO: 5), negative sense (reverse) 5'-TCGTCATTACTG AATTTCAACA-3' (SEQ ID NO:4), and negative sense (reverse) 5'-CATGCTCTTAGT CACTTGACCCTA-3' (SEQ ID NO:6), or complements thereof, or mixtures thereof. The DNA sequence of the probe utilized in the TaqMan PCR is 5'-CGGTAGGGCGAA GAAACCAACACC-3' (SEQ ID NO:7).

The detection of amplified gene product in the sample is evidence of the presence of *A. avenae* subspecies in the biological sample. When combined with BIO-PCR, the method is useful in diagnosing presence of viable cells of *A. avenae*. One set of primers, primers identified by SEQ ID NO:1 and SEQ ID NO:2, is useful in a detection assay to identify that *A. avenae* is present in a sample; specifically, that any one or all of the subspecies, *A. avenae* subsp. *avenae, A. avenae* subsp. *cattleyae*, or *A. avenae* subsp. *citrulli,* are present. The primer set comprising SEQ ID NO:1 and SEQ ID NO:2 cannot distinguish the subspecies *avenae, cattleyae,* and *citrulli;* however, the primer set identified by SEQ ID NOS: 1 and 2, can be used to screen for the presence of these organisms. The primer set comprising SEQ ID NO:3 and SEQ ID NO:4 distinguishes *A. avenae* subsp. *citrulli* from *A. avenae* subsp. *avenae* and *cattleyae*. When the advantages of the BIO-PCR are combined with the specificity of SEQ ID NO:3 and SEQ ID NO:4 for *A. avenae* subsp. *citrulli,* the sensitivity and specificity for detecting the pathogen responsible for watermelon fruit blotch is further enhanced.

Detection utilizing the BIO-PCR method is enhanced still further when combined with the TaqMan detection system. When the primer set comprising SEQ ID NO:5 with either SEQ ID NO:4 or SEQ ID NO:6 is utilized in a combined BIO-PCR and TaqMan method, such methodology results in the detection of as few as 2 cfu/ml. Thus, there is no loss of sensitivity as compared to BIO-PCR and Southern analysis. Two important advantages of the TaqMan system are (1) that measurement of real-time hybridization is rapid and (2) that the hybridization product is the definitive, irrefutable product of the polymerization chain reaction. Further, the methodology involved in the assay process makes possible the handling of large numbers of samples efficiently and without cross-contamination and is therefore adaptable for robotic sampling. The advantages of rapid, conclusive data together with labor and cost efficiency make the combination BIO-PCR and TaqMan detection system utilizing the specific primers of the invention a highly beneficial system for monitoring seed pathogens, especially in those circumstances where seed screening results have major commercial and trade consequences.

The screening for *A. avenae* subsp. *avenae, cattleyae*, and *citrulli,* using the primer set consisting of SEQ ID NO:1 and SEQ ID NO:2, can be followed by a detection assay utilizing the primer set consisting of SEQ ID NO:3 and SEQ ID NO:4 in order to specifically detect the presence of *A. avenae* subsp. *citrulli.* Furthermore, in such screening assays, where a detection assay utilizing a primer set identified by SEQ ID NO:1 and SEQ ID NO:2 is followed by a detection assay utilizing a primer set identified by SEQ ID NO:3 and SEQ ID NO:4, a negative result in the detection assay utilizing the primer set consisting of SEQ ID NO:3 and SEQ ID NO:4 is indicative of either or both *A. avenae* subsp. *avenae* or *cattleyae* being present and that *A. avenae* subsp. *citrulli* is not present. Similarly, where a detection assay utilizing a primer set identified by SEQ ID NO:1 and SEQ ID NO:2 is followed by a TaqMan detection assay utilizing the primer set comprising SEQ ID NO:5 together with either SEQ ID NO:4 or SEQ ID NO:6, a negative result in the second detection assay, utilizing SEQ ID NO:5 together with SEQ ID NO:4 or 6, is indicative of either or both *A. avenae* subsp. *avenae* or *cattleyae* being present and that *A. avenae* subsp. *citrulli is not present.*

The primers and amplification method can further be useful for evaluating and monitoring the efficacy of any treatments utilized to eliminate the pathogenic *A. avenae* subspecies. In this method, biological samples are obtained from seeds prior to treatment and from seeds which have undergone treatment with a treatment protocol such as hot water or household bleach, designed to eradicate *A. avenae* subspecies. In addition, biological samples can be obtained from seeds at several time points during treatment. DNA amplification products of a target sequence of *A. avenae* from all samples are analyzed for the presence of *A. avenae*. Results from samples obtained prior, during and after treatment are compared in order to determine efficacy of the treatment protocol.

Similarly, the novel primers and methods are very useful for epidemiology and host-pathogen studies. A further advantage of using BIO-PCR is that quantitative data on viable pathogen populations can be obtained by dilution-end-point analysis if samples are not heavily contaminated with saprophytes in those instances when quantitation of propagules would be desirable.

EXAMPLES

Example 1

Bacterial cultures

Bacteria were extracted from healthy seeds of rice and watermelon by soaking 1000–2000 seeds in 0.02% Tween 20 solution (ratio of 5 ml/g) for 4 hr at 4° C. Aliquots of 100 $\mu$l were pipetted onto each of ten plates of King et al.'s medium B (KB), nutrient agar (NA), yeast extract-dextrose calcium carbonate (YDC), or a semiselective agar medium such as neutral red semiselective medium (Schaad. 1988. Laboratory Guide for Identification of Plant Pathogenic Bacteria, 2nd Ed., APS Press, St. Paul, Minn.) for *A. avenae* subsp. *avenae* or EBB for *A. avenae* subsp. *citrulli,* and the suspension spread with a L-shaped glass rod. Five plates were washed three times with 1.0 ml of 10 mM Tris-HCl solution (pH 7.4) after 48 hrs incubation at 36° C. for BIO-PCR as described (Schaad et al. 1995, supra) and the sample archived at −20° C. The remaining five plates were read for visible suspect colonies after three and four days. Suspect colonies were cloned and stored on YDC slants at room temperature for pathogenicity tests. These bacteria do not store well at 2–40° C.

The strains and source of Acidovorax and other bacteria used in this study are shown in Table 1. Cultures were maintained on YDC or KB agars at room temperature and stored at −85° C. Colony morphology of *A. avenae* strains were checked on YDC and KB media and accumulation of Poly-β-hydroxybytyrate determined as described (Schaad. 1988, supra). Colonies of all strains received as *A. avenae* subsp. *avenae* (including *P. rubrilineans, P. setariae,* and *P. rubrisubalbicans*) were non-fluorescent on KB medium, round convex morphology and tan in color on YDC medium. Colonies of *A. avenae* subsp. *citrulli,* subsp. *konjaci,* and ATCC strain 33619 of subsp. *cattleyae* had colonies indistinguishable from *A. avenae* subsp. *avenae*. All these strains were positive for Poly-β-hydroxybutyrate. In contrast, morphologies of strains PC107, 112, and 145 of subsp. *cattleyae* were very different and these strains did not accumulate Poly-β-hydroxybutyrate. We therefore concluded that these cultures were contaminants and not subsp. *cattleyae*. Final identity of all *A. avenae* subsp. *avenae* strains was confirmed by inoculating oat and corn seedlings, as described (Schaad et al. 1975, supra) and the identity of all strains of *A. avenae* subsp. *citrulli* were confirmed by inoculating watermelon seedlings (Schaad et al. 1978, supra).

Example 2

Extraction of genomic DNA

Cells were grown in Luria-Bertain (LB) liquid medium overnight on a rotary shaker at 30° C. Cell suspensions were centrifuged, suspended in 10 mM Tris-HCl solution (pH 8.0), and adjusted to a concentration of 0.1 OD at $A_{600}$. Suspensions of cells or single colonies growing on YDC or KB medium were used for PCR-amplification without prior DNA extraction or other sample processing. Genomic DNA was extracted from washed cells, as described (Prosen et al., supra).

Example 3

Design of Primers

The ISR was amplified using primers R16-1 and R23-2R and genomic DNA of *A. avenae* subsp. *avenae* strain COA1 and *A. avenae* subsp. *citrulli* strain 29625, utilizing the method described by Kim et al., supra. The amplified product was electrophoresed in a 2% Metaphore gel (FMA BioProducts, Rockland, Md., USA). The resulting target DNA band was excised from the gel and processed for loading in agarose, following the suppliers recommendations. For *A. avenae* subsp. *avenae*, the DNA of strain COA1 was blunt ended using T4 DNA polymerase, and ligated to plasmid vector pGEM-7Zf(+) (Promega, Madison, Wis., USA), and digested with SmaI, using T4 DNA Ligase. The ligation products were used to transform DH5 competent cells (Life Technologies, Md., USA) according to suppliers recommendations. For *A. avenae* subsp. *citrulli,* the gel-purified product was ligated into pCR2.1 with TA cloning kit (INVITROGEN) following the suppliers protocols.

For *A. avenae* subsp. *avenae*, the amplified full length 950-bp product of ISR was cloned into pGEM7f (GIBCO BRL). The resulting clone, pOA3, containing a 950-bp insert of full length ISR, was then sequenced. For *A. avenae* subsp. *citrulli,* the amplified full length 950-bp product of ISR was cloned into pCR2.1 with TA cloning kit (INVITROGEN). The resulting clone, pCIT7, containing a 950-bp insert of full length ISR, was then sequenced.

Chemicals and antibiotics were purchased from Sigma Chemical Co. (St. Louis, Mo.), restriction and DNA modifying enzymes were purchased from Life Technologies (Bethesda, Md.), and all supplies for PCR were purchased from Perkin Elmer (Norwalk, Calif.).

Example 4

Sequence analysis

The sequencing of the cloned 16S-23S ISR fragment was performed by the dideoxy-chain termination method using ABI PRISM 310 Genetic Analyzer and Dye Terminator Cycle Sequencing Core Kit (Perkin Elmer, Foster City, Calif.) following the manufacturer's protocol (Sanger et al., supra). The size of the ISR fragment of *A. avenae* subsp. *avenae* sequenced was 625 bp (FIG. 1B; Aaa, shaded). The fragment had a GC content of 48.87%, and a single $tRNA^{Ala}$ gene of 73 bp. The size of the sequenced ISR fragment of *A. avenae* subsp. *citrulli* was 617 bp, (FIG. 1B, Aac, shaded). It had a GC content of 48.94%, and the same single $tRN^{Ala}$ gene. The sequences were first aligned by using the DNASES program (Hitachi SEQ, Ltd.) and the alignments were corrected manually. This ISR sequence contained a single copy of $tRNA^{Ala}$. By comparing the gene sequence of *A. avenae* subsp. *avenae* to the primers for *Leuconostoc oenos* (Zavaleta et al. 1996. *Microbiol.* 142: 2105–2114), *Streptococcus aureus* (Gurtler et al. 1995 *Microbiol.* 141: 1255–1265), *Bacillus subtilis* (Loughney et al. 1982. *Nuc. Acids Res.* 10: 1607–1624) and *E. coli* (Harvey et al. 1988. *J. Bacteriol.* 170: 1235–1238), the primers SEQ ID NO:1 and SEQ ID NO:2 for *A. avenae* subsp. *avenae* and SEQ ID NO:3 and SEQ ID NO:4 for *A. avenae* subsp. *citrulli* were selected (FIG. 1A, FIG. 1B). From the ISR sequences, candidate primers SEQ ID NO:1 and SEQ ID NO:2 were selected using the program OLIGO (National Biosciences, Hamel, Minn.) and synthesized commercially by GIBCO BRL (Frederick, Md.).

Minor errors of PCR and sequencing reactions were eliminated by sequencing both strands from two independently cloned fragments of separate PCR experiments. No sequence variability between the two 16S-23S ISR copies was found.

Example 5

Polymerase Chain Reaction

Primers were screened for specificity in 25 μl reactions containing 2–5 μl of the bacterial cell suspensions, 200 μM each of dNTPs, 0.16 μM of each primer, 1×PCR reaction buffer II and 1.0 U of AMPLITAQ Gold polymerase (Perkin Elmer). All amplifications were conducted in a Perkin Elmer 9600 thermocycler (Perkin Elmer Cetus, Norwalk, CT). For primers having SEQ ID NO:1 and SEQ ID NO:2, the amplifications were conducted with an initial DNA denaturation at 94° C. for 30 S; 55° C. for 30 S; 72° C. for 1 min and a final extension step of 7 min at 72° C. For the primers of SEQ ID NO:3 and SEQ ID NO:4, the amplifications were conducted with an initial DNA denaturation at 94° C. for 10 min followed by 5 cycles of 94° C. for 30 S; 56° C. for 30 S; 72° C. for 1 min, then 25 cycles of 94° C. for 45 S; 72° C. for 45 S; 72° C. for 1 min and a final extension step as above. To detect a product, 5 to 10 μl of the reaction were electrophoresed on 1.2% agarose gels and stained with ethidium bromide as described (Maniatis et al. 1989. Molecular Cloning, a Laboratory Manual. Cold Spring Harbor Laboratory, Cold Spring Harbor, N.Y.).

The primers having SEQ ID NO:1 and SEQ ID NO:2 of *A. avenae* subsp. *avenae* and SEQ ID NO:3 and SEQ ID NO:4 of *A. avenae* subsp. *citrulli* were used to amplify the ISR comprising a target sequence of DNA of 43 strains of *A. avenae*, 11 strains of *A. avenae* subsp. *citrulli,* four of *A. avenae* subsp. *cattleyae*, single strains of *A. avenae* subsp. *konjaci* and *A. facilis,* 26 other known bacteria, and 27 unknown bacteria isolated from seeds. The specificity of each set of primers is illustrated in Table 1. For primers having SEQ ID NO:1 and SEQ ID NO:2, a PCR product of approximately 550 bp was obtained for all strains of *A. avenae* subsp *avenae* and *A. avenae* subsp. *citrulli* and the ATCC strain of *A. avenae* subsp. *cattleyae.* Three strains of *A. avenae* subsp. *cattleyae* and the single strain of *A. avenae* subsp. *konjaci* were negative. All other bacteria, including 1–6 strains each of five other species of non-fluorescent pseudomonads (including 12 strains of Burkholderia), four fluorescent pseudomonads, two xanthomonads, two erwinea, and six strains of unknown bacteria from rice seed were negative. Primers having SEQ ID NO:3 and SEQ ID NO:4 produced a 450-bp product with all strains of *A. avenae* subsp. *citrulli* specifically; all other bacteria were negative (Table 1 and FIG. 2B).

Example 6

Selection of primers and probes for TaqMan PCR

Primer and fluorescent probe sequences for the TaqMan PCR assay were designed with the Primer Design software program from the manufacturer (PE Applied Biosystems, Foster City, Calif.) using the sequences: SEQ ID NO:4, SEQ ID NO:5, SEQ ID NO:6. Several combinations of forward (F) and reverse (R) primer and TaqMan probe (SEQ ID NO:7) sequences were tested for their performance as determined by Cycle Threshold (Ct) values. Ct value is defined as the PCR cycle number at which the signal of the probe rises above background. The lower the Ct value, the better the PCR performance. TaqMan reactions were analyzed for 40–45 cycles using an ABI Prism 7700 Sequence detection System (PE Applied Biosystems) following methods recommended by the manufacturer. Dilutions of cells or DNA of *A. avenae* subsp. *citrulli* and water (negative control) were measured.

To determine inherent sensitivity and Ct values of TaqMan and *A. avenae* subsp. *citrulli* primers (SEQ ID NO:4, SEQ ID NO:5, and SEQ ID NO:6), a titration using 1 to 100,000 pg from four replicates of five- and ten-fold dilutions of purified genomic DNA from *A. avenae* subsp. *citrulli* was performed. Under the same PCR cycling conditions for classical and BIO-PCR, ten-fold serial dilutions of $10^{-6}$ of a liquid NBY culture of *A. avenae* subsp. *citrulli* were prepared. For classical TaqMan PCR, aliquots of 14 μl of dilutions of $10^{-3}$, $10^{-4}$, $10^{-5}$, and $10^{-6}$ were tested in duplicate. For BIO-PCR, aliquots of 100 μl of the same dilutions were plated onto 8 plates each of KB, NA, YDC, and neutral red semiselective media. After 72 hrs, four plates were washed, as described in Example 1, and four kept for determining the number of cfu's of *A. avenae* subsp. *citrulli* on KB, NA, YDC, and neutral red semiselective media agar media after 4 and 7 days.

Example 7

Specificity and sensitivity of primers

Figure 3:
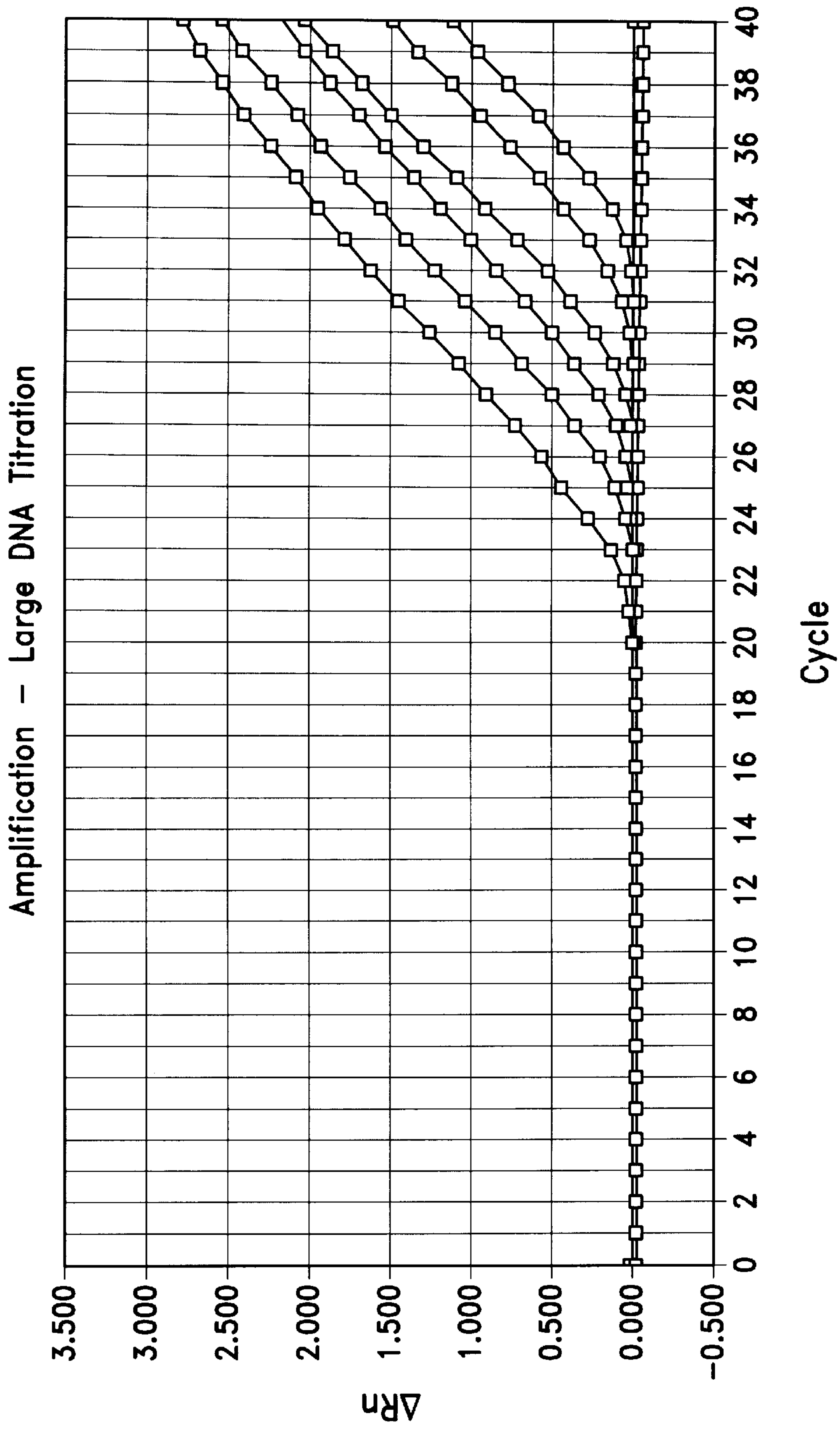
FIG. 3 shows the amplification plot from the TaqMan PCR method where the accumulation of the fluorescent signal from reporter dye molecules is monitored at each PCR cycle for dilutions of DNA from *A. avenae* subsp. *citrulli* utilizing the primers SEQ ID NO: 5 and SEQ ID NO:4 and the probe SEQ ID NO:7. The concentrations of DNA shown are left to right: E5, 1000 pg; E6, 500 pg; E7, 100 pg; E8, 50 pg; E9, 10 pg; E10, 5 pg; E11, 1 pg; and E12, water control, (baseline).

Forward primer 5'-CCTCCACCAACCAATACGCT-3' (SEQ ID NO: 5), reverse primer 5'-TCGTCATTACTGAATTTCAACA-3' (SEQ ID NO:4), and TaqMan probe 5'-CGGTAG GGCGAAGAAACCAACACC (SEQ ID NO:7) resulted in a Ct value of 14.62, the lowest Ct value for 100,000 pg DNA. The next lowest Ct value, 15.40, was observed when forward primer 5'-CCTCCACCAACCAATACGCT-3' (SEQ ID NO: 5), reverse primer 5'-CATGCTCTTAGTCACTTGACCCTA-3' (SEQ ID NO:6), and TaqMan probe 5'-CGGTAG GGCGAAGAAACCAACACC (SEQ ID NO:7) were utilized. FIG. 3 shows the best primers. All other primers had much higher Ct values (Table 2). Utilizing the best two primer sets; SEQ ID NOs: 5&4 and 5&6, the DNA titration results show that fluorescence rises above background after 33 and 37 cycles, respectively, for 1 pg DNA. FIG. 3 shows a typical titration curve for the primer set SEQ ID NOs:5 and 4. Suspensions of *A. avenae* subsp. *citrulli* containing around 10 cfu/ml were consistently positive by classical TaqMan PCR. Washings of plates of KB, NA, YDC, and neutral red semiselective media containing 1–2 colonies of *A. avenae* subsp. *citrulli* were consistently positive by TaqMan BIO-PCR.

TABLE 2

Selection of primers and probe combinations for TaqMan PCR

| Primers & | Whole Cell Titrations (Dilutions) | | | | | |
|---|---|---|---|---|---|---|
| Probe Set | Ct(-2) | Ct(-4) | Ct(-6) | Rn(-2) | Rn(4) | Rn(-6) |
| AACF2/ AACR2 AaP1 | 28.84 | 30.30 | 40.00 | 1.05 | 0.27 | 0.00 |
| AACF2/ AACR4 AaP1 | 24.22 | 31.02 | 37.95 | 2.17 | 0.88 | 0.20 |
| SEQ ID NOs: 5,4 7 | 16.27 | 23.02 | 30.98 | 3.07 | 2.50 | 1.30 |
| SEQ ID NOs: 5,6 7 | 17.79 | 22.81 | 32.39 | 3.13 | 2.21 | 0.71 |

| Primers & | DNA Titration (Ct Values) | | | | | | | |
|---|---|---|---|---|---|---|---|---|
| Probe Set | 100,000 | 50,000 | 10,000 | 1,000 | 100 | 10 | 1 | 0 |
| AACF2/ AACR4 AaP1 | 20.78 | 21.20 | 23.15 | 26.87 | 31.54 | 36.99 | 37.83 | 40 |
| SEQ ID NOs: 5,4 7 | 14.62 | 14.93 | 16.95 | 20.58 | 25.18 | 28.82 | 33.83 | 40 |
| SEQ ID NOs: 5,6 7 | 15.40 | 15.81 | 18.06 | 22.43 | 27.40 | 31.75 | 37.62 | 40 |

The forward primer 5'-CCTCCACCAACCAATACGCT-3' (SEQ ID NO: 5) and the reverse primer of 5'-TCGTCATTACTGAATTTCAACA-3' (SEQ ID NO: 4) of *A. avenae* subsp. *citrulli* were used to amplify the ISR of 16 strains of *A. avenae* subsp. *avenae*, 11 strains of *A. avenae* subsp. *citrulli*, a single strain of *A. facilis*, 18 strains of pseudomonads, four xanthomonads, and two flavobacteria. For these primers, an amplified fluorescent signal was obtained with all strains of *A. avenae* subsp. *citrulli* specifically; all other bacteria were negative, as illustrated in Table 3.

TABLE 3

Species and strains and results of PCR with primers SEQ ID NOS: 5 & 4 of *A. avenae* subsp. *citrulli.*

| Organism | Origin | PCR Amplification SEQ ID NOS: 5 & 4[a] |
|---|---|---|
| *A. avenae* subsp. *avenae* | | |
| Fc 158 ATCC 40582 E1 | Denmark | – |
| Fc 159 ATCC 40580 | Denmark | – |
| Fc 160 391226 | Denmark | – |
| Fc 172 ATCC 40582 A1 | Denmark | – |
| Fc 189 301507 | Japan | – |
| Fc 190 301508 | Japan | – |
| Fc 191 301511 | Japan | – |
| Fc 192 311058 | Japan | – |
| Fc 193 301509 | Japan | – |
| Fc 194 301510 | Japan | – |

TABLE 3-continued

Species and strains and results of PCR with primers SEQ ID NOS: 5 & 4 of *A. avenae* subsp. *citrulli.*

| Organism | Origin | PCR Amplification SEQ ID NOS: 5 & 4[a] |
|---|---|---|
| Fc 195 311057 | Japan | – |
| Fc 196 311056 | Japan | – |
| Fc 197 301506 | Japan | – |
| Fc 198 301504 | Japan | – |
| Fc 199 301503 | Japan | – |
| Fc 200 301502 | Japan | – |
| *A. avenae* subsp. *citrulli* | | |
| Fc 141 AaC-H1B | California | + |
| Fc 181 AaC H17 | California | + |
| Fc 201 8408 | Purdue | + |
| Fc 203 AaC 2576 | California | + |
| Fc 204 AaC 2578 | California | + |
| Fc 247 ATCC | | + |
| Fc 248 AaC 206 | California | + |
| Fc 249 | Natural seed isolate Lot 2573 | + |
| Fc 250 | Natural seed isolate Lot 2573 | + |
| Fc 251 | Natural seed isolate Lot 2573 | + |
| Fc 253 | Natural seed isolate Lot 2573 | + |
| *A. facilis* | | |
| Fc 208 ATCC 6230 | | – |
| *Pseudomonas pseudoalicaligenes* subsp. *pseudoalicaligenes* | | |
| Fc 206 ATCC 26550 | | – |
| *P. aptata* | | |
| Fc 218 8545 | Ukraine | – |
| *P. wieringae* | | |
| Fc 219 7921 | Ukraine | – |
| Fc 220 7923 | Ukraine | – |
| *P. panici* | | |
| Fc 221 7963 | Ukraine | – |
| Fc 222 7963* | Ukraine | – |
| *P. xanthochlora* | | |
| Fc 223 8538 | Ukraine | – |
| Fc 224 8540 | Ukraine | – |
| *P. lupini* | | |
| Fc 225 8532 | Ukraine | – |
| Fc 226 8533 | Ukraine | – |
| *P. solancearum* | | |
| Fc 228 AW1 | Georgia | – |
| Fc 229 AW1-PC | Georgia | – |
| *P. rubrisalbicans* | | |
| Fc 97 PR108 | | – |
| Fc 98 PR110 | | – |
| *P. syringae* pv. syringae | | |
| Fc 103 301D | Steve Hutchinson | – |
| Fc 108 B 728a | Wisconsin | – |
| *P. fluorescens* | | |
| Fc 117 4SI-14 | Auburn, AL | – |
| Fc 118 4SI-15 | Auburn, AL | – |
| *Xanthomonas albilineans* | | |
| Fb 581 Xa 15009 (G53) | Guadeloupe | – |
| Fb 582 Xa 150010 (MDG 58) | Madagascar | – |
| Fb 616 Xa 93-170 | Canal Point, FL | – |

TABLE 3-continued

Species and strains and results of PCR with primers SEQ ID NOS: 5 & 4 of *A. avenae* subsp. *citrulli.*

| Organism | Origin | PCR Amplification SEQ ID NOS: 5 & 4[a] |
|---|---|---|
| *X. cucurbitae* | | |
| Fb 1054 | Frederick | – |
| *Flavobacterium balustinum* | | |
| Fb 1081 ATCC 53198 | Columbus, OH | – |
| *Flavobacterium* sp. | | |
| Fb 1082 ATCC 39723 | Crawford | – |

[a]Positive result means presence of an amplified fluorescent signal from the reporter dye molecule and negative means no fluorescent signal.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An oligonucleotide primer consisting of the sequence 5'-GTCGGTGCTAAC GACATGG-3' (SEQ ID NO:1).

2. An oligonucleotide primer consisting of the sequence 5'-AGACATCTCCGCTTTCTTTCAA-3' (SEQ ID NO:2).

3. A primer set comprising oligonucleotides consisting of the sequences 5'-GTCGGTGCTAACGACATGG-3' (SEQ ID NO:1) and 5'-AGACATCTCCGCTTTCTTTCAA-3' (SEQ ID NO:2).

4. An oligonucleotide primer consisting of the sequence 5'-GGAAGAATTCGGTG CTACCC-3' (SEQ ID.NO:3).

5. An oligonucleotide primer consisting of the sequence 5'-TCGTCATTACTGAATTTC AACA-3' (SEQ ID NO:4).

6. A primer set comprising oligonucleotides consisting of the sequences 5'-GGAAGA ATTCGGTGCTACCC-3' (SEQ ID NO: 3) and 5'-TCGTCATTACTGAATTTCAACA-3' (SEQ ID NO:4).

7. An oligonucleotide primer consisting of the sequence 5'-CCTCCACCAACCAA TACGCT-3' (SEQ ID NO:5).

8. An oligonucleotide primer consisting of the sequence 5'-CATGCTCTTAGTCACTTG ACCCTA-3' (SEQ ID NO:6).

9. A primer set comprising oligonucleotides consisting of the sequences 5'-CCTCCACC AACCAATACGCT-3' (SEQ ID NO:5) and 5'-TCGTCATTACTGAATTTCAACA-3' (SEQ ID NO:4).

10. A primer set comprising oligonucleotides consisting of the sequences 5'-CCTCCAC CAACCAATACGCT-3' (SEQ ID NO:5) and 5'-CATGCTCTTAGTCACTTGACCCTA-3' (SEQ ID NO:6).

11. An oligonucleotide probe consisting of the sequence 5'-CGGTAGGGCGAAGAA ACCAACACC-3' (SEQ ID NO:7).

12. An intergenic spacer region (ISR) sequence selected from the group consisting of: ISR1 of *A. avenae* subsp. *citrulli* comprising the nucleotides 58–694 of SEQ ID NO:8 and ISR2 of *A. avenae* subsp. *avenae* comprising the nucleotides 59–682 of SEQ ID NO:9.

13. A method of detecting the presence of Acidovorax by polymerase chain reaction, said method comprising:

a) providing the DNA of said Acidovorax or a test sample of cells or microorganisms suspected of containing the DNA of said Acidovorax;

b) amplifying a target sequence of DNA of said Acidovorax using at least one primer selected from the group consisting of the oligonucleotide 5'-GTCGGTGCT AACGACATGG-3' (SEQ ID NO:1), the oligonucleotide 5'-AGACATCTCCGCT TTCTTTCAA-3' (SEQ ID NO:2), the oligonucleotide 5'-CGGTGCTACCC-3' (SEQ ID NO:3), the oligonucleotide 5'-TCGTCATTACTGAATTTCAACA-3' (SEQ ID NO:4); the oligonucleotide 5'-CCTCCACCAACCAATACGCT-3' (SEQ ID NO:5), and the oligonucleotide 5'-CATGCTCTTAGTCACTTGACCCTA-3' (SEQ ID NO:6); and c) detecting the presence of the amplification products of the target sequence of DNA as an indication of the presence of Acidovorax.

14. A method of detecting the presence of Acidovorax by polymerase chain reaction, said method comprising:

a) providing the DNA of said Acidovorax or a test sample of cells or microorganisms suspected of containing the DNA of said Acidovorax;

b) amplifying a target sequence of DNA of said Acidovorax using a primer set selected from the group consisting of (I) a primer set comprising oligonucleotides consisting of the sequence 5'-GTCGGTGCTAACGACATGG-3' (SEQ ID NO:1) and the sequence 5'-AGACATCTCCGCTTTCTTTCAA-3' (SEQ ID NO:2), (ii) a primer set comprising oligonucleotides consisting of the sequence 5'-GGAAGA ATTCGGTGCTACCC-3' (SEQ ID NO: 3) and the sequence 5'-TCGTCATTACTG AATTTCAACA-3' (SEQ ID NO:4); (iii) a primer set comprising oligonucleotides consisting of the sequence 5'-CCTCCACCAACCAATACGCT-3' (SEQ ID NO:5) and the sequence 5'-TCGTCATTACTGAATTTCAACA-3' (SEQ ID NO:4); and (iv) a primer set comprising oligonucleotides consisting of the sequence 5'-CCT CCACCAACCAATACGCT-3' (SEQ ID NO:5) and the sequence 5'-CATGCTCTT AGTCACTTGACCCTA-3' (SEQ ID NO:6); and c) detecting the presence of the amplification products of the target sequence of DNA as an indication of the presence of Acidovorax.

15. The method of claim 14, wherein said Acidovorax is *A. avenae* subsp. *avenae* , *A. avenae* subsp. *catteyae,* or *A. avenae* subsp. *citrulli,* and the primer set comprises oligonucleotides consisting of the sequence 5'-GTCGGTGCTAACACATGG-3' (SEQ ID NO:1) and the sequence 5'-AGACATCTCCGCTTTCTTTCAA-3' (SEQ ID NO:2).

16. The method of claim 14, wherein said Acidovorax is *Acidovorax citrulli* and the primer set is selected from the group consisting of (a) the primer set comprising oligonucleotides consisting of the sequence 5'-GGAAGAATTCGGTGCTACCC-3' (SEQ ID NO: 3) and the sequence 5'-TCGTCATTACTGAATTTCMCA-3' (SEQ ID NO:4); (b) the primer set comprising oligonucleotides consisting of the sequence 5'-CCTCCACC AACCAATACGCT-3' (SEQ ID NO:5) and the sequence 5'-TCGTCATTACTGAATTTC AACA-3' (SEQ ID NO:4);

and (c) the primer set comprising oligonucleotides consisting of the sequence 5'-CCTCCACCAACCAATACGCT-3' (SEQ ID NO:5) and the sequence 5'-CATGCTCTTAGTCACTTGACCCTA-3' (SEQ ID NO:6).

17. The method of claim 13, 14, 15, or 16 wherein the polymerase chain reaction (PCR) is a BIO-PCR, wherein the test sample consists essentially of viable cells or microorganisms or the DNA extracted from said viable cells or microorganisms, and wherein said test sample results from (a) culturing said viable cells or microorganisms on agar plates or in liquid medium in order to expand the number of said viable cells or microorganisms, (b) collecting the viable cells or microorganisms expanded by culturing, by either washing the plates of plated samples or collecting aliquots from liquid culture, and (c) washing the viable cells or microorganisms by filtration, centrifugation, or other conventional means.

18. The method of claim 13, 14, 15, or 16 wherein the polymerase chain reaction (PCR) is a BIO-PCR; wherein the test sample consists essentially of viable cells or microorganisms or the DNA extracted from said viable cells or microorganisms; wherein said test sample results from (a) culturing said viable cells or microorganisms on agar plates or in liquid medium in order to expand the number of said viable cells or microorganisms, (b) collecting the viable cells or microorganisms expanded by culturing, by either washing the plates of plated samples or collecting aliquots from liquid culture, and (c) washing the viable cells or microorganisms by filtration, centrifugation, or other conventional means; and wherein the presence of the amplification products is detected by the TaqMan system.

19. The method of claim 17 wherein the agar is EBB medium.

20. The method of claim 18 wherein the agar is EBB medium.

21. The method of screening for particular subspecies of *A. avenae*, said method comprising:

a) providing the DNA of said Acidovorax or a test sample of cells or microorganisms suspected of containing the DNA of said Acidovorax;

b) amplifying a target sequence of DNA of said Acidovorax using a primer set comprising oligonucleotides consisting of the sequence 5'-GTCGGTGCTAACGA CATGG-3' (SEQ ID NO:1) and the sequence 5'-AGACATCTCCGCTTTCTTT CAA-3' (SEQ ID NO:2);

c) detecting the presence of the amplification products of the target sequence of DNA as an indication of the presence of *A. avenae* subsp. *avenae, A. avenae* subsp. *catteyae,* or *A. avenae* subsp. *citrulli;* d) providing the test sample for which it has been determined that any one or all of the subspecies, *A. avenae* subsp. *avenae, A. avenae* subsp. *cattleyae*, or *A. avenae* subsp. *citrulli*, are present in the test sample;

e) amplifying a target sequence of DNA using a primer set selected from the group consisting of (I) the primer set comprising oligonucleotides consisting of the sequence 5'-GGAAGAATTCGGTGCTACCC-3' (SEQ ID NO: 3) and the sequence 5'-TCGTCATTACTGMTTTCAACA-3' (SEQ ID NO:4); (ii) the primer set comprising oligonucleotides consisting of the sequence 5'-CCTCCACC AACCAATACGCT-3' (SEQ ID NO:5) and the sequence 5'-TCGTCATTACTGAAT TTCAACA-3' (SEQ ID NO:4); and (iii) the primer set comprising oligonucleotides consisting of the sequence 5'-CCTCCACCAACCAATACGCT-3' (SEQ ID NO:5) and the sequence 5'-CATGCTCTTAGTCACTTGACCCTA-3' (SEQ ID NO:6); and f) determining the presence or absence of amplification products of the target DNA and, as an indication thereby, in the presence of the DNA amplification products, specifically distinguishing *A. avenae* subsp. *citrulli* from *A. avenae* subsp. *avenae* and *cattleyae*, or in the absence of the amplification products, determining that either or both *A. avenae* subsp. *avenae* or *cattleyae* are present and that *A. avenae* subsp. *citrulli* is not present.

22. The method of claim 21 wherein the polymerase chain reaction (PCR) is a BIO-PCR, wherein the test sample consists essentially of viable cells or microorganisms or the DNA extracted from said viable cells or microorganisms, and wherein said test sample results from (a) culturing said viable cells or microorganisms on agar plates or in liquid medium in order to expand the number of said viable cells or microorganisms, (b) collecting the cells or microorganisms expanded by culturing, by either washing the plates of plated samples or collecting aliquots from liquid culture, and (c) washing the viable cells or microorganisms by filtration, centrifugation, or other conventional means.

23. The method of claim 22 wherein the presence of the amplification products is detected by the TaqMan system.

24. A method of evaluating or monitoring the efficacy of treatments utilized to eliminate pathogenic *A. avenae* subspecies from a seed lot, said method comprising:

a) providing the DNA of said Acidovorax or a test sample of cells or microorganisms suspected of containing the DNA of said Acidovorax;

b) amplifying a target sequence of DNA of said Acidovorax according to the method of any one of claims 13–16, to provide DNA amplification products of Acidovorax;

c) detecting the presence of the amplification products of the target sequence of DNA as an indication of the presence of Acidovorax in the first test sample, if present;

d) treating the seed lot from which the first test sample is obtained, or a test portion of said seed lot, with a composition to reduce or eradicate Acidovorax;

e) providing a second test sample from the substance undergoing treatment to reduce or eradicate *A. avenae* subspecies;

f) amplifying a target sequence of DNA of said Acidovorax according to the method of any one of claims 13–16, to provide DNA amplification products of Acidovorax;

g) detecting the amount of the amplification products of the target sequence of DNA in said second test sample; and h) comparing the amount of amplification products or absence of amplification products in the second test sample to the amount of amplification products detected in the first test sample in step (c), as an indication of whether or not the treatment protocol has been successful in reducing or eradicating *A. avenae.*

25. The method of claim 24 wherein the polymerase chain reaction (PCR) is a BIO-PCR, wherein the test sample consists essentially of viable cells or microorganisms or the DNA extracted from said viable cells or microorganisms, and wherein said test sample results from (a) culturing said viable cells or microorganisms on agar plates or in liquid medium in order to expand the number of said viable cells or microorganisms, (b) collecting the cells or microorganisms expanded by culturing, by either washing the plates of plated samples or collecting aliquots from liquid culture, and (c) washing the viable cell microorganisms by filtration, centrifugation, or other conventional means.

26. The method of claim 25 wherein the presence of the amplification products is detected the TaqMan system.

27. The method of any one of claims 24–26, wherein the second test samples are obtained at real time points during the treatment protocol.

28. A kit for identifying a subspecies of *A. avenae*, comprising at least one primer from the group consisting of the oligonucleotide 5'-GTCGGTGCTAACGACATGG-3' (SEQ ID NO:1), the oligonucleotide 5'-AGACATCTCCGCTTTCTTTCAA-3' (SEQ ID NO:2), the oligonucleotide 5'-GGAAGAATTCGGTGCTACCC-3' (SEQ ID NO:3), the oligonucleotide 5'-TCGTCATTACTGAATTTCAACA-3' (SEQ ID NO:4), the oligonucleotide 5'-CCTCCACCAACCAATACGCT-3' (SEQ ID NO:5) and the oligonucleotide 5'-CATGCT CTTAGTCACTTGACCCTA-3' (SEQ ID NO:6).

29. A kit for identifying a subspecies of *A. avenae*, wherein the subspecies is *A. avenae* subsp. *avenae, A. avenae* subsp. *cattleyae*, or *A. avenae* subsp. *citrulli,* comprising a primer set consisting of the oligonucleotides 5'-GTCGGTGCTAACGA CATGG-3' (SEQ ID NO:1) and 5'-AGACATCTCCGCTTTCTTTCAA-3' (SEQ ID NO:2).

30. A kit for identifying *A. avenae* subsp. *citrulli,* comprising a primer set selected from the group consisting of (a) the primer set comprising oligonucleotides consisting of the sequence 5'-GGAAGAATTCGGTGCTACCC-3' (SEQ ID NO: 3) and the sequence 5'-TCGTCATTACTGAATTTCAACA-3' (SEQ ID NO:4); (b) the primer set comprising oligonucleotides consisting of the sequence 5'-CCTCCACCAACCAATACGCT-3' (SEQ ID NO:5) and the sequence 5'-TCGTCATTACTGMTTTCAACA-3' (SEQ ID NO:4); and (c) the primer set comprising oligonucleotides consisting of the sequence 5'-CCT CCACCAACCAATACGCT-3' (SEQ ID NO:5) and the sequence 5'-CATGCTCTTAGT CACTTGACCCTA-3' (SEQ ID NO:6).

* * * * *

UNITED STATES PATENT AND TRADEMARK OFFICE

CERTIFICATE OF CORRECTION

PATENT NO. : 6,146,834
DATED : November 14, 2000
INVENTOR(S) : Schaad et al.

It is certified that error appears in the above-identified patent and that said Letters Patent is hereby corrected as shown below:

Claim 16(a),
Line 63, "SEQ ID NO:4" should read -- 5'-TCGTCATTACTGAATTTCAACA-3' --

Claim 21(e),
Line 62, "SEQ ID NO:4" should read -- 5'-TCGTCATTACTGAATTTCAACA-3' --

Claim 30(b),
Line 17, "SEQ ID NO:4" should read -- 5'-TCGTCATTACTGAATTTCAACA-3' --

Signed and Sealed this

Fourth Day of December, 2001

*Attest:*

Nicholas P. Godici

NICHOLAS P. GODICI

*Attesting Officer*

*Acting Director of the United States Patent and Trademark Office*

SEQUENCE LISTING

```
<160> NUMBER OF SEQ ID NOS: 9

<210> SEQ ID NO 1
<211> LENGTH: 19
<212> TYPE: DNA
<213> ORGANISM: Acidovorax avenae

<400> SEQUENCE: 1

gtcggtgcta acgacatgg                                                  19


<210> SEQ ID NO 2
<211> LENGTH: 22
<212> TYPE: DNA
<213> ORGANISM: Acidovorax avenae

<400> SEQUENCE: 2

agacatctcc gctttctttc aa                                              22


<210> SEQ ID NO 3
<211> LENGTH: 20
<212> TYPE: DNA
<213> ORGANISM: Acidovorax avenae subsp. citrulli

<400> SEQUENCE: 3

ggaagaattc ggtgctaccc                                                 20


<210> SEQ ID NO 4
<211> LENGTH: 22
<212> TYPE: DNA
<213> ORGANISM: Acidovorax avenae subsp. citrulli

<400> SEQUENCE: 4

tcgtcattac tgaatttcaa ca                                              22


<210> SEQ ID NO 5
<211> LENGTH: 20
<212> TYPE: DNA
<213> ORGANISM: Acidovorax avenae subsp. citrulli

<400> SEQUENCE: 5
```

-continued

```
cctccaccaa ccaatacgct                                              20


<210> SEQ ID NO 6
<211> LENGTH: 24
<212> TYPE: DNA
<213> ORGANISM: Acidovorax avenae subsp. citrulli

<400> SEQUENCE: 6

catgctctta gtcacttgac ccta                                         24


<210> SEQ ID NO 7
<211> LENGTH: 24
<212> TYPE: DNA
<213> ORGANISM: Acidovorax avenae subsp. citrulli

<400> SEQUENCE: 7

cggtagggcg aagaaaccaa cacc                                         24


<210> SEQ ID NO 8
<211> LENGTH: 747
<212> TYPE: DNA
<213> ORGANISM: Acidovorax avenae subsp. citrulli

<400> SEQUENCE: 8

ggtgaagtcg taacaaggta gccgtatcgg aaggtgcggc tggatcacct cctttctgga     60

aaacagcatt caatattgaa cgcccactct tatcggttgt tggaagaatt cggtgctacc    120

cgacatgggt ctggtagctc agctggttag agcaccgtct tgataaggct ggggtcgttg    180

gttcgagccc aactagaccc accaaatctt ccgaacataa gatgcgagga tcagtggggg    240

attagctcag ctgggagagc acctgctttg caagcagggg gtcgtcggtt cgatcccgtc    300

atcctccacc aaccaatacg ctctgcggta gggcgaagaa accaacacca aagcggcttc    360

gcgagaggcc tctttgttgt tggtccggta tagaccggat caatcggctg ttctttaaaa    420

attcatagag tcgaatcagc gttgccggcg gaaagcagga aactgcaccg tgccgccggt    480

gacaaaaatt tgattgcgtc aaaacgaata ttcaattgag cgaaagcttg ttgaaattca    540

gtaatgacga attgttctct aggtagcaat accgcaagaa gaattcacat tacggcataa    600

cgcgcgaagt gaaagacctc gcaagtcctt gaaagaaagc ggagatttct cgctagagat    660

ttcaaagttt tagggtcaag tgactaagag catgtggtgg atgccttggc gatgataggc    720

gacgaaagac gtgatagcct gcgataa                                      747


<210> SEQ ID NO 9
<211> LENGTH: 753
<212> TYPE: DNA
<213> ORGANISM: Acidovorax avenae subsp. avenae

<400> SEQUENCE: 9

ggtgaagtcg taacaaggta gccgtatcgg aaggtgcggc tggatcacct cctttctaag     60

gaaaacagca ttcaatattg aacgcccaca cttatcggtt gttggaagaa gtcggtgcta    120

acgacatggg tctgtagctc agctggttag agcaccgtct agataaggcg gggagtcgtt    180

gggttcgagc ccaactcgac ccaccaaatc ttccgaacat aagatgcgag gaatcaagtg    240

ggggattagc tcagctggga gagcacctgc tttgcaagca gggggtcgtc ggttcgatcc    300

cgtcatcctc cacccaacca atatgtcctg cggtagggca aagaaactaa caccaaagcg    360

gcttcgcgaa gaggcctctt tgttgttggt ccggtataga ccgggtcaat cggctgttct    420
```

-continued

```
ttaaaaattc atagagtcga atcagcgttg ccggcggaaa gcaggaaact gcatccgtgc    480

cgtcggcaac aaaaatttga ttgcgtccaa acgaatattc aattggagcg aaagctgatc    540

gaaattcagt aatgacgaat tgttctctta ggtagcaata cccgaagaag aattacacat    600

tacggcatta acgcgcgatg tgaaagacct cgcaagtcct tgaaagaaag cggagatgtc    660

tcgcaagaga tgtcaagtta taggtcaagt gactaagagc atgtggtgga tccttgcgat    720

gatagcgacg aaagacgtga tagcctgcga taa                                 753
```